United States Patent [19]

Hasegawa et al.

[11] Patent Number: 4,760,165

[45] Date of Patent: Jul. 26, 1988

[54] RECOVERING USEFUL COMPONENTS AT LEAST CONTAINING DIMETHYL TEREPHTHALATE FROM HIGH-BOILING BYPRODUCTS OCCURRING IN THE PRODUCTION OF DIMETHYL TEREPHTHALATE

[75] Inventors: Hideo Hasegawa; Takao Fujii, both of Matsuyama, Japan

[73] Assignee: Teijin Petrochemical Industries, Ltd., Tokyo, Japan

[21] Appl. No.: 928,300

[22] Filed: Nov. 10, 1986

[30] Foreign Application Priority Data

Nov. 13, 1985 [JP] Japan ................................. 60-252633
Feb. 21, 1986 [JP] Japan ................................. 61-35363

[51] Int. Cl.$^4$ ............................................. C07C 67/48
[52] U.S. Cl. ........................................ 560/78; 203/38; 203/66; 562/412
[58] Field of Search ......................... 562/412; 560/78; 203/38, 66

[56] References Cited

U.S. PATENT DOCUMENTS 4,092,481 5/1978 Bunger .................................. 560/77
4,096,340 6/1978 Fujii et al. ............................ 560/77
4,126,755 11/1978 Bunger et al. ........................ 560/77

Primary Examiner—Werren B. Lone
Assistant Examiner—Vera C. Clarke
Attorney, Agent, or Firm—Sherman and Shalloway

[57] ABSTRACT

A method of recovering useful components at least containing dimethyl terephthalate from high-boiling byproducts occurring in the production of dimethyl terephthalate, which comprises oxidizing p-xylene and/or methyl p-toluate with a molecular oxygen-containing gas in the presence of a heavy metal oxidation catalyst, subjecting the resulting oxidation product to esterification with methanol, separating dimethyl terephthalate and esters having lower boiling points than dimethyl terephthalate from the esterification reaction product by distillation, and thereafter treating the distillation residue containing byproducts having higher boiling points than dimethyl terephthalate with methanol to recover at least dimethyl terephthalate from the treated product; wherein the treatment of the distillation residue with methanol is carried out at a temperature of 110° to 240° C. under a pressure sufficient to maintain methanol in the liquid phase.

11 Claims, No Drawings

RECOVERING USEFUL COMPONENTS AT LEAST CONTAINING DIMETHYL TEREPHTHALATE FROM HIGH-BOILING BYPRODUCTS OCCURRING IN THE PRODUCTION OF DIMETHYL TEREPHTHALATE

This invention relates to a method of recovering useful components at least containing dimethyl terephthalate from high-boiling byproducts occurring in the production of dimethyl terephthalate.

More specifically, this invention relates to a method of recovering useful components such as dimethyl terephthalate, methyl p-toluate or methyl p-hydroxymethylbenzoate from high-boiling byproducts occurring in the process of producing dimethyl terephthalate by oxidizing p-xylene and/or methyl p-toluate and esterifying the oxidation product with methanol.

A method has heretofore been known to produce dimethyl terephthalate which comprises oxidizing p-xylene and/or methyl p-toluate with a molecular oxygen-containing gas in the presence of a heavy metal oxidation catalyst and then esterifying the oxidation product with methanol (see, for example, British Pat. Nos. 809,730 and 1,313,083).

It is also known to recover useful components such as dimethyl terephthalate from high-boiling byproducts occurring during distillation of dimethyl terephthalate from the esterification reaction product. Japanese Patent Publication No. 20303/1981 and the corresponding German Offenlegungsschrift No. P2327773.8 describe a method in which high-boiling byproducts having a boiling point higher than dimethyl terephthalate which occur in the production of dimethyl terephthalate by oxidizing p-xylene and/or methyl p-toluate with a molecular oxygen-containing gas in the presence of a heavy metal oxidation catalyst and then esterifying the oxidation product with methanol are contacted with methanol to recover useful components from the high-boiling byproducts. The patent documents state that the contacting of the high-boiling byproducts with methanol is carried out at a temperature in the range of 260° to 400° C.

U.S. Pat. No. 4,126,755 and the corresponding German Offenlegungsschrift P2244662.4 disclose a method of producing dimethyl terephthalate from high-boiling tarry residues resulting from the combined oxidation of p-xylene and methyl p-toluate with air, esterification of the resulting acids with methanol and after-treatment of the esterification reaction product, which comprises treating the high-boiling residues with methanol at a temperature above 250° C., and thereafter separating the resulting dimethyl terephthalate in accordance with conventional separation techniques.

Since in the aforesaid methods, the high-boiling residues are treated with methanol at temperatures higher than the critical temperature of methanol (i.e., about 240° C.), it is seen that the treatment is carried out in the vapor phase.

U.S. Pat. No. 4,092,481 and the corresponding German Offenlegungsschrift No. P2427875.9 disclose a method of producing dimethyl terephthalate and intermediate products of the dimethyl terephthalate manufacture from the high-boiling byproducts obtained during the air oxidation of p-xylene and methyl p-toluate in the liquid phase, subsequent esterification of the resulting acids and separation of the so-produced esters, which comprises treating the high-boiling byproducts with methanol at an elevated temperature and then separating the resultant product by distillation with the addition of a carrier such as methanol. The patent documents state that the treatment of the byproducts with methanol at an elevated temperature is carried out at a temperature of 180° to 370° C. and a pressure of 0 to 60 atms-G. However, nowhere in these documents is there a description that this methanol treatment is carried out under such conditions that liquid methanol is present in the treating system.

It is an object of this invention therefore to provide a method of recovering useful components containing dimethyl terephthalate from high-boiling byproducts of the dimethyl terephthalate production which comprises treating the byproducts with methanol in the liquid phase.

Another object of this invention is to provide a method of effectively recovering useful components containing dimethyl terephthalate from high-boiling byproducts of the dimethyl terephthalate production, which comprises treating the high-boiling byproducts with methanol at a relatively low temperature, thereby minimizing formation of byproducts during the methanol treatment.

Still another object of this invention is to provide a recovery method in which useful components containing dimethyl terephthalate can be separated industrially advantageously in high yields even from high-boiling byproducts of the dimethyl terephthalate production which contain fairly large amounts of dimethyl terephthalate or p-methylbenzyl p-toluate because the treating temperature is relatively low and the formation of byproducts is minimized during the methanol treatment.

Yet another object of this invention is to provide a recovery method in which after the methanol treatment, the loss of useful components during the distillation operation is suppressed by removing the heavy metal oxidation catalyst normally contained in the high-boiling byproducts, and thereafter recovering useful components such as dimethyl terephthalate by distillation.

Further objects and advantages of this invention will become apparent from the following description.

According to this invention, these objects and advantages of the invention are achieved by a method of recovering useful components at least containing dimethyl terephthalate from high-boiling byproducts occurring in the production of dimethyl terephthalate, which comprises oxidizing p-xylene and/or methyl p-toluate with a molecular oxygen-containing gas in the presence of a heavy metal oxidation catalyst, subjecting the resulting oxidation product to esterification with methanol, separating dimethyl terephthalate and esters having lower boiling points than dimethyl terephthalate from the esterification reaction product by distillation, and thereafter treating the distillation residue containing byproducts having higher boiling points than dimethyl terephthalate with methanol to recover at least dimethyl terephthalate from the treated product; wherein the treatment of the distillation residue with methanol is carried out at a temperature of 110° to 240° C. under a pressure sufficient to maintain methanol in the liquid phase.

The distillation residue containing higher boiling byproducts than dimethyl terephthalate which is to be treated with methanol in accordance with the method of this invention is obtained by oxidizing p-xylene and- /or methyl p-toluate with a molecular oxygen-containing gas in the presence of a heavy metal oxidation catalyst, subjecting the resulting oxidation product to esterification with methanol, and separating dimethyl terephthalate and esters having lower boiling points than dimethyl terephthalate from the esterification reaction product by distillation. The distillation residue may be the bottoms as obtained, or may be subjected to recrystallization or further distillation before use to remove most of useful components such as dimethyl terephthalate.

The step of oxidizing p-xylene and/or methyl p-toluate with a molecular oxygen-containing gas in the presence of a heavy metal oxidation catalyst can be carried out in accordance with methods known per se. For example, the oxidation step can be carried out in accordance with the method described in British Pat. No. 1,313,083. Specifically, p-xylene and/or methyl p-toluate, particularly a mixture of p-xylene and methyl p-toluate in a weight ratio of from 2:1 to 1:4, is oxidized in the liquid phase with a molecular oxygen-containing gas at a temperature of 140° to 240° C. in the presence of a heavy metal oxidation catalyst consisting essentially of a first component which is manganese metal, a manganese compound soluble in the reaction system, or a mixture thereof, and a second component which is cobalt metal, a cobalt compound soluble in the reaction system, or a mixture thereof.

Preferably, in the heavy metal oxidation catalyst, the gram-atomic ratio of manganese metal to cobalt metal is from 0.1:99.9 to 99:1 when the components are calculated as manganese metal and cobalt metal respectively, and the concentration of the catalyst is adjusted so that when the components are calculated as metal, their total weight is 50 to 1500 ppm by weight based on the total weight of the reaction system.

The resulting oxidation product is then subjected to esterification with methanol. Dimethyl terephthalate and esters having lower boiling points than dimethyl terephthalate are separated from the esterification reaction product by distillation.

The separation of dimethyl terephthalate and useful intermediate products such as methyl p-toluate and methyl p-formylbenzoate from the methyl esterification product by distillation has heretofore been practiced by normally maintaining the bottom temperature of the distillation column at 200° to 240° C., at the highest 250° C. under a reduced pressure of 50 to 200 mmHg.

The reason for separating the useful products, composed mainly of dimethyl terephthalate by reduced pressure distillation as above is to facilitate separation of dimethyl terephthalate while preventing conversion of the metal component in the oxidation catalyst to the metal oxide or free metal, particularly at high temperatures. Such a metal oxide or free metal deposits on the heat-transfer surfaces of a heat-exchanger to reduce the heat-transfer efficiency and cause clogging. Obviously, the use of excessively high temperatures for separation of dimethyl terephthalate by distillation is thermally uneconomical.

The present inventors have found that by treating the distillation residue containing high boiling byproducts with methanol at a temperature of 110° to 240° C. under a pressure sufficient to maintain methanol in the liquid phase, useful products such as dimethyl terephthalate, methyl p-toluate, methyl p-hydroxymethylbenzoate and p-methylbenzyl alcohol are obtained in high yields while minimizing formation of byproducts during the treatment.

The treatment with methanol is carried out under a sufficient pressure to maintain methanol in the liquid phase. Preferably, the pressure employed is 4 to 90 kg/cm$^2$-G, especially preferably 10 to 70 kg/cm$^2$-G.

The method of this invention has the advantage of being able to minimize formation of byproducts during the treatment with methanol since the methanol treatment is carried out at a relatively low temperature under a pressure sufficient to maintain methanol in the liquid phase.

The treatment with methanol is carried out at a temperature of 110° to 240° C., preferably 135° to 235° C.

The methanol may be not only purified methanol, but also other forms of methanol, for example, the mother liquor used in recrystallizing crude dimethyl terephthalate. Preferably, methanol is used in an amount at least 0.1 times, for example 0.25 to 4 times, the weight of the high-boiling byproducts to be treated. If the amount of methanol used is less than 0.1 times, the amount of the useful components tends to decrease abruptly. If it is more than 10 times, the amount of the useful components does not tend to increase appreciably.

The suitable range of the time required for the treatment with methanol varies depending upon the reaction temperature, etc. For example, the treatment is usually carried out for a period of about 0.1 to 10 hours.

The treatment with methanol can be carried out either batchwise or continuously.

The high-boiling distillation residue to be treated can be used in a form containing the heavy metal oxidation catalyst used in the oxidation. This obviates the need for performing a procedure of removing the heavy metal catalyst and enables the treatment with methanol to proceed more smoothly. Needless to say, it is possible to remove the heavy metal catalyst from the high-boiling distillation residue, and treat the residue with methanol with or without the addition of a known esterification catalyst or a known ester interchange catalyst. The reaction mixture which has undergone the methanol treatment is then subjected to distillation. Advantageously, the reaction mixture is first subjected to flash distillation to remove the excess of methanol and then to reduced pressure distillation to give a distillate at least containing dimethyl terephthalate as a useful component. The flash distillation and the reduced pressure distillation are known as unit operations, and in the method of this invention, too, they are carried out in accordance with the known operations. The method of this invention has the advantage of being able to drastically decrease expenditures that go into the facilities and utility cost since the useful components can be recovered by the method of this invention without employing a special distillation such as steam distillation or carrier distillation as in the prior art.

Investigations of the present inventors have shown that instead of subjecting the reaction mixture which has undergone the methanol treatment to the aforesaid series of distillation, the useful components can be advantageously obtained in higher yields by (i) removing methanol from the reaction mixture by, for example, flash distillation, (ii) extracting the distillation residue with water to remove the heavy metal oxidation catalyst from the oxidation step which is present in the reaction mixture, and (iii) thereafter recovering a distillate at least containing dimethyl terephthalate by distillation, for example reduced pressure distillation.

The flash distillation in step (i) is carried out at a temperature of 180° C. at the highest, preferably 160° C. at the highest, in order to prevent side reactions during distillation which lead to a drastic decrease in the amount of the useful components recovered.

The extraction with water in step (ii) is usually carried out at 80° to 180° C. The amount of water used is preferably 0.5 to 10 times the weight of the distillation residue to be extracted. Preferably, the extraction is carried out with stirring at the aforesaid temperature at which the distillation residue to be treated is maintained in the liquid phase. After the extraction, water is subjected to layer separation and removed. The heavy metal catalyst from the oxidation step can be recovered from the aqueous layer in a customary manner. The activity of the recovered heavy metal catalyst is greater than the activity of the heavy metal catalyst directly recovered from the high-boiling byproducts before the methanol treatment although no clear reason has yet been able to be assigned to it.

According to the method of this invention described above, useful components such as dimethyl terephthalate, methyl p-toluate, methyl p-hydroxymethylbenzoate and p-methylbenzyl alcohol can be recovered from the high-boiling byproducts. These useful components may be recycled to the dimethyl terephthalate producing process, or may be purified to recover them as products.

The following examples illustrate the method of this invention in greater detail.

EXAMPLE 1

A mixture of p-xylene and methyl p-toluate was oxidized continuously with air in the liquid phase at a predetermined temperature and pressure in the presence of a catalyst comprising cobalt and manganese. The resulting oxidation product containing p-toluic acid and monomethyl terephthalate as main components is esterified with methanol. The esterification product was then distilled under reduced pressure to separate it into a distillate containing crude dimethyl terephthalate and methyl p-toluate as main components and a ditillation residue containing 15% by weight of dimethyl terephthalate and high-boiling byproducts. This distillation residue also contained 0.9% by weight of p-methylbenzyl p-toluate.

One hundred grams of the distillation residue thus obtained and 100 g of methanol were introduced into a 500 ml titanium autoclave equipped with a stirrer. After the inside of the autoclave was purged with nitrogen, the mixture was maintained for 1 hour at a temperature of 230° C. and a pressure of 49 kg/cm$^2$-G with stirring.

After the reaction, the reaction product was taken out, and methanol was evaporated on a hot water bath. The residue was distilled under a reduced pressure of 20 mmHg to give 32.6 g of dimethyl terephthalate, 4.5 g of methyl p-toluate, 11.6 g of methyl p-hydroxymethylbenzoate, 2.2 g of p-methylbenzyl alcohol, 0.6 g of methyl p-formylbenzoate and 0.1 g of p-tolualdehyde.

EXAMPLES 2-5 AND COMPARATIVE EXAMPLE 1

Example 1 was repeated except that the amount of methanol, the reaction temperature and the reaction time were changed as indicated in Table 1. The amounts of useful components recovered are shown in Table 1.

EXAMPLE 6

The distillation residue used in Example 1 was extracted with water at 95° C. to remove cobalt and manganese and adjust the contents of cobalt and manganese to 18 ppm and 1 ppm respectively. The residue was dried at 110° C. The resulting distillation residue with lower cobalt and manganese contents was reacted and the useful components were recovered in the same way as in Example 1 except that the reaction temperature was changed to 2 hours. The results are indicated in Table 1.

COMPARATIVE EXAMPLE 2

The same distillation residue as used in Example 1 (150 g) was charged into the same autoclave as used in Example 1, and 150 g/hr of methanol and 60 liters/hr of nitrogen gas were continuously fed for 4 hours at 290° C. and 28 kg/cm$^2$-G. The methanol vapor was withdrawn continuously, and after the pressure in the autoclave was returned to atmospheric pressure, condensed by a condenser.

After the reaction, the reaction product in the autoclave and the condensed methanol were combined, and subjected to the same operation as in Example 1 to give 46.1 g of dimethyl terephthalate (DMT), 7.0 g of methyl p-toluate (MPT), 6.5 g of methyl p-hydroxymethylbenzoate (MHB), 1.1 g of p-methylbenzyl alcohol and 0.8 g of methyl p-formylbenzoate.

TABLE 1

| | Ex. 2 | Ex. 3 | Ex. 4 | Ex. 5 | Ex. 6 | CEx. 1 |
|---|---|---|---|---|---|---|
| Reaction conditions | | | | | | |
| Reaction temperaure (°C.) | 230 | 230 | 165 | 180 | 230 | 270 |
| Reaction pressure (kg/cm$^2$ — G) | 38 | 64 | 18 | 24 | 49 | 70 |
| Reaction time (hours) | 1 | 1 | 3 | 2 | 2 | 2 |
| Amount of methanol (g) | 50 | 400 | 200 | 200 | 100 | 78 |
| Amounts of the useful components recovered (g) | | | | | | |
| DMT | 32.1 | 34.1 | 32.4 | 32.5 | 31.2 | 28.9 |
| MPT | 4.3 | 4.9 | 4.3 | 4.5 | 2.5 | 4.8 |
| MHB | 10.2 | 13.2 | 11.4 | 11.3 | 14.3 | 4.5 |
| Others | 3.0 | 3.5 | 2.9 | 3.0 | 2.5 | 1.7 |
| Total | 49.6 | 55.7 | 51.0 | 51.3 | 50.5 | 39.9 |

Ex. = Example;
CEx. = Comparative Example

EXAMPLE 7

A mixture of p-xylene and MPT was oxidized with air continuously in the liquid phase in the presence of a catalyst containing Co and Mn. The resulting oxidation product contained p-toluic acid and monomethyl terephthalate as main components. The oxidation product was esterified with methanol. The esterification reaction product was distilled under reduced pressure to separate it into a distillate containing DMT and MPT as main components and a distillation residue containing high-boiling byproducts, 17% by weight of DMT and 0.25% by weight of Co.

A 500 ml titanium autoclave equipped with a stirrer was charged with 100 g of the distillation residue and 100 g of methanol. The inside of the autoclave was purged with nitrogen, and the mixture was maintained for 1 hour at 230° C. and 49 kg/cm$^2$-G with stirring.

The reaction product was withdrawn and methanol was evaporated from it on a hot water bath. After evaporation of methanol, the residue was maintained at the same temperature for 30 minutes and stirred at 95° C. for 1 hour with an equal weight of acidic byproduct water from the DMT producing process. Subsequently, the mixture was left to stand at the same temperature for 1 hour to separate the aqueous layer. The organic layer was dried at 110° C.

Thereafter, this reaction product hardly containing the catalyst (Co+Mn<50 ppm) was distilled under 20 mmHg to give 34.6 g of DMT, 4.7 g of MPT, 16.3 g of MHB, 2.9 g of p-methylbenzyl alcohol (MBA), 0.6 g of methyl p-formylbenzoate (AE) and 0.1 g of p-tolualdehyde (PTAL).

EXAMPLE 8 AND COMPARATIVE EXAMPLE 3

Example 7 was repeated except that the amount of methanol, the reaction temperature and the reaction time were changed as indicated in Table 2. The results are shown in Table 2.

EXAMPLE 9

Example 7 was repeated except that methanol was evaporated at 200° C. from the reaction product. The results are shown in Table 2.

COMPARATIVE EXAMPLE 4

The same distillation residue as used in Example 7 (150 g) was charged into the same autoclave as used in Example 7, and 150 g/hr of methanol and 60 liters/hr of nitrogen gas were continuously fed at 290° C. and 28 kg/cm$^2$-G for 4 hours. The methanol vapor was continuously withdrawn, and after returning the pressure to atmospheric pressure, was condensed with a condenser.

After the reaction, the autoclave was cooled to 210° C., and the pressure was returned to atmospheric pressure at 210° C. via an adjusting valve. Methanol which was evaporated was condensed in the same way as above. After pressure releasing, the methanol vapor at 210° C. was introduced into the autoclave under atmospheric pressure at 210° C. for 4 hours at a rate of 150 g/hr. The vapor that left the autoclave was condensed. On a hot water bath methanol was evaporated from the condensed product to give 46.2 g of DMT, 6.5 g of MPT, 8.0 g of MHB, 1.3 g of MBA and 0.7 g of AE.

TABLE 2

|  | Ex. 8 | CEx. 3 | Ex. 9 |
| --- | --- | --- | --- |
| Reaction conditions |  |  |  |
| Reaction temperature (°C.) | 165 | 270 | 230 |
| Reaction pressure (kg/cm$^2$ − G) | 18 | 70 | 49 |
| Reaction time (hours) | 3 | 2 | 1 |
| Amount of methanol (g) | 200 | 78 | 100 |
| Methanol evaporation temperature (°C.) | 100 | 100 | 200 |
| Amounts of the useful components recovered (g) |  |  |  |
| DMT | 34.0 | 31.0 | 34.3 |
| MPT | 4.3 | 4.8 | 4.7 |
| MHB | 15.9 | 10.6 | 11.4 |
| MBA + AE + PTAL | 3.5 | 1.9 | 2.0 |
| Total | 57.7 | 48.3 | 52.4 |

Ex. and CEx.: Same as the footnote to Table 1.

What is claimed is:

1. A method of recovering useful components at least containing dimethyl terephthalate from high-boiling byproducts occurring in the production of dimethyl terephthalate, which comprises oxidizing p-xylene and/or methyl p-toluate with a molecular oxygen-containing gas in the presence of a heavy metal oxidation catalyst, subjecting the resulting oxidation product to esterification with methanol, separating dimethyl terephthalate and esters having lower boiling points than dimethyl terephthalate from the esterification reaction product by distillation, and thereafter treating the distillation residue containing byproducts having higher boiling points than dimethyl terephthalate with methanol to recover at least dimethyl terephthalate from the treated product; wherein the treatment of the distillation residue with methanol is carried out at a temperature of 110° to 240° C. under a pressure sufficient to maintain methanol in the liquid phase.

2. The method of claim 1 wherein the distillation residue is treated with 0.1 to 10 times its weight of methanol.

3. The method of claim 1 wherein the distillation residue is treated at a temperature in the range of 135° to 235° C.

4. The method of claim 1 wherein the distillation residue is treated under a pressure sufficient to maintain methanol in the liquid phase which is between 4 to 90 kg/cm$^2$-G.

5. The method of claim 1 wherein the distillation residue to be treated with methanol contains the heavy metal oxidation catalyst.

6. The method of claim 1 wherein in the oxidation step, a mixture of p-xylene and methyl p-toluate in a weight ratio of from 2:1 to 1:4 is oxidized with a molecular oxygen-containing gas in the liquid phase at a temperature of 140° to 240° C. in the presence of a heavy metal oxidation catalyst consisting essentially of a first component which is manganese metal, a manganese compound soluble in the reaction system, or a mixture thereof and a second component which is cobalt metal, a cobal compound soluble in the reaction system, or a mixture thereof.

7. The method of claim 6 wherein the gram-atomic ratio of manganese metal to cobalt metal is from 0.1:99.9 to 99:1 when the components are calculated as manganese metal and cobalt metal respectively, and the concentration of the catalyst is adjusted so that when the components are calculated as metal, their total weight is 50 to 1500 ppm by weight based on the total weight of the reaction system.

8. A method of recovering useful components at least containing dimethyl terephthalate from high-boiling byproducts occurring in the production of dimethyl terephthalate, which comprises oxidizing p-xylene and/or methyl p-toluate with a molecular oxygen-containing gas in the presence of a heavy metal oxidation catalyst, subjecting the resulting oxidation product to esterification with methanol, separating dimethyl terephthalate and esters having lower boiling points than dimethyl terephthalate from the esterification reaction product by distillation, and thereafter treating the distillation residue containing byproducts having higher boiling points than dimethyl terephthalate with methanol to recover at least dimethyl terephthalate from the treated product; wherein the treatment of the distillation residue with methanol is carried out at a temperature of 110° to 240° C. under a pressure sufficient to maintain methanol in the liquid phase while the distillation residue contains the heavy oxidation catalyst, the excess of methanol is removed by distillation, the residue is extracted with water to remove the heavy metal oxidation catalyst substantially, and a distillate at least containing dimethyl terephthalate is recovered by distillation.

9. The method of claim 8 wherein the excess of methanol is evaporated at a temperature of not more than 180° C.

10. The method of claim 8 wherein the extraction with water is carried out at a temperature of 80° to 180° C.

11. The method of claim 8 wherein the distillation performed to recover the distillate at least containing dimethyl terephthalate is reduced pressure distillation.

* * * * *